(12) United States Patent
Manalis et al.

(10) Patent No.: US 7,282,329 B2
(45) Date of Patent: Oct. 16, 2007

(54) SUSPENDED MICROCHANNEL DETECTORS

(75) Inventors: Scott Manalis, Cambridge, MA (US); Thomas Burg, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/669,883

(22) Filed: Sep. 23, 2003

(65) Prior Publication Data

US 2005/0064581 A1 Mar. 24, 2005
US 2007/0172940 A9 Jul. 26, 2007

Related U.S. Application Data

(63) Continuation-in-part of application No. 10/336,549, filed on Jan. 2, 2003.

(60) Provisional application No. 60/405,184, filed on Aug. 22, 2002.

(51) Int. Cl.
*C12Q 1/68* (2006.01)
*C12M 1/36* (2006.01)
*G01N 15/06* (2006.01)
*C07H 21/04* (2006.01)

(52) U.S. Cl. .................... 435/6; 435/283.1; 435/287.2; 435/287.3; 435/288.5; 422/68.1; 536/23.1

(58) Field of Classification Search .................. 435/6, 435/174, 283.1, 287.2, 288.5; 536/23.1; 422/68.1
See application file for complete search history.

(56) References Cited

U.S. PATENT DOCUMENTS

| 4,896,966 | A | * | 1/1990 | Boisseau et al. ............ 382/128 |
|---|---|---|---|---|
| 5,742,377 | A | | 4/1998 | Minne et al. |
| 5,883,705 | A | | 3/1999 | Minne et al. |
| 5,982,534 | A | * | 11/1999 | Pinkel et al. ............... 359/387 |
| 6,002,131 | A | | 12/1999 | Manalis et al. |
| 6,075,585 | A | | 6/2000 | Minne et al. |
| 6,156,216 | A | | 12/2000 | Manalis et al. |
| 6,307,202 | B1 | | 10/2001 | Manalis et al. |
| 6,337,479 | B1 | * | 1/2002 | Kley .......................... 250/234 |
| 6,473,187 | B1 | | 10/2002 | Manalis |
| 6,477,901 | B1 | | 11/2002 | Tadigadapa et al. ... 73/861.352 |
| 6,942,169 | B2 | * | 9/2005 | Sparks ......................... 241/1 |
| 2002/0137084 | A1 | | 9/2002 | Quate et al. |
| 2003/0000291 | A1 | | 1/2003 | Kolosov et al. |

(Continued)

OTHER PUBLICATIONS

Albrecht, et al., "Frequency Modulation Detection using High-Q Cantilevers for Enhanced Force Microscope Sensitivity", *J. Appl. Phys.* 69(2): 668-673, 1991.

(Continued)

*Primary Examiner*—B J Forman
(74) *Attorney, Agent, or Firm*—Stacy L. Blasberg; Sam Pasternack; Choate Hall & Stewart, LLP

(57) ABSTRACT

An apparatus for detecting an analyte in solution that has a suspended beam containing at least one microfluidic channel containing a capture ligand that bonds to or reacts with an analyte. The apparatus also includes at least one detector for measuring a change in the beam upon binding or reaction of the analyte. A method of making the suspended microfluidic channels is disclosed, as well as, a method of integrating the microfluidic device with conventional microfluidics having larger sample fluid channels.

24 Claims, 11 Drawing Sheets

U.S. PATENT DOCUMENTS

| | | | |
|---|---|---|---|
| 2003/0027351 | A1 | 2/2003 | Manalis et al. |
| 2003/0027354 | A1* | 2/2003 | Geli .......................... 436/178 |
| 2003/0073071 | A1 | 4/2003 | Fritz et al. |
| 2004/0038426 | A1 | 2/2004 | Manalis |

OTHER PUBLICATIONS

Anczykowski, et al., "Analysis of the Interaction Mechanisms in Dynamic Mode SFM by Means of Experimental Data and Computer Simulation", *Appl. Phys. A*. 66: S885-S889, 1998.

Berenschot, et al., "Advanced Sacrificial Poly-Si Technology For Fluidic Systems", *J. Micromech. Microeng.* 12: 621-624, 2002.

Chen, et al., "Noncovalent Functionalization of Carbon Nanotubes for Highly Specific Electronic Biosensors", *PNAS*, 100(9): 4984-4989, 2003.

Cheng, et al., "Localized Silicon Fusion and Eutectic Bonding for MEMS Fabrication and Packaging", *Journal of Microelectromechanical Systems*, 9(1): 3-8, 2000.

Cui, et al., "Nanowire Nanosensors for Highly Sensitive and Selective Detection of Biological and Chemical Species", *Science*, 293: 1289-1292, 2001.

deBoer, et al., "Micromachining of Buried Micro Channels in Silicon", *Journal of Microelectromechanical Systems*, 9(1): 94-103, 2000.

Duffy, et al., "Rapid Prototyping of Microfluidic Systems in Poly(dimethylsiloxane)", *Anal. Chem.* 70: 4974-4984, 1998.

Duffy, et al., "Rapid Prototyping of Microfluidic Switches in Poly(Dimethyl Siloxane) and Their Actuation by Electro-Osmotic Flow", *J. Micromech. Microeng.* 9: 211-217, 1999.

Enoksson, et al., "Fluid Density Sensor Based on Resonance Vibration", *Sensors and Actuators A*: 327-331, 1995.

Enoksson, et al., "Vibration Modes of a Resonant Silicon Tube Density Sensor", *Journal of Microelectromechanical Systems*, 5(1): 39-44, 1996.

Fritz, et al., "Electronic Detection of DNA by its Intrinsic Molecular Charge", *PNAS*, 99(22): 14142-14146, 2002.

Fritz, et al., "Translating Biomolecular Recognition into Nanomechanics", *Science*, 288: 316-318, 2000.

Garra, et al., "Dry Etching of Polydimethylsiloxane for Microfluidic Systems", *J. Vac. Sci. Technol. A*. 20(3): 975-982, 2002.

Harendt, et al., "Silicon Fusion Bonding and its Characterization", *J. Micromech. Microeng*, 2: 113-116, 1992.

Inoue, et al., "Characteristics of New Dielectric Isolation Wafers for High Voltage Power IC's by Single-Si Poly-Si Direct Bonding (SPSDB) Technique", *IREE Transactions on Electron Devices*, 42(2): 356-358, 1995.

Ismail, et al., "Polysilicon and Titanium Disilicide, Polycide Fusion Bonding for 3-D Microdevices Applications", 86-89, no date provided.

Jackman, et al., Microfluidic Systems with On-Line "UV Detection Fabricated in Photodefinable Epoxy", *J. Micromech. Microeng*. 11: 263-269, 2001.

Jo, et al., "Three-Dimensional Micro-Channel Fabrication in Plydimethylsiloxane (PDMS) Elastomer", *Journal of Microelectromechanical Systems*, 9(1): 76-81, 2000.

Juncker, et al., "Soft and Rigid Two-Level Microfluidic Networks for Patterning Surfaces", *J. Micromech. Microeng*. 11: 532-541, 2001.

Khoury, et al., "Ultra Rapid Prototyping of Microfluidic Systems Using Liquid Phase Phtopolymerization", *Lab Chip*, 2: 50-55, 2002.

Koh, et al., "Investigations in Polysilicon CMP to Apply in Sub-Quarter Micron DRAM Device", *IEEE*, 214-217, 1999.

Lang, et al., "Sequential Position Readout from Arrays of Micromechanical Cantilever Sensors", *Appl. Phys. Lett.* 72(3): 383-385, 1998.

Lange, et al., "CMOS Resonant Beam Gas Sensing System with On-Chip Self Excitation", 547-552, 2001.

Lukosz, W., "Integrated Optical Chemical and Direct Biochemical Sensors", *Sensors and Actuators*, B29: 37-50, 1995.

Maute, et al., "Detection of Volatile Organic Compounds (VOCs) with Polymer-Coated Cantilevers", *Sensors and Actuators B*, 58: 505-511, 1999.

Pan, et al., "A Low-Temperature Wafer-Bonding Technique Using Patternable Materials", *J. Micromech. Microorg.* 12: 611-615, 2002.

Plöβl, et al., "Wafer Direct Bonding: Tailoring Adhesion Between Brittle Materials", *Materials Science and Engineering*, R25: 1-88, 1999.

Rasmussen, et al.,"Fabrication Techniques to Realize CMOS-Compatible Microfluidic Microchannels", *Journal of Microelectromechanical Systems*, 10(2): 286-297, 2001.

Raiteri, et al., "Micromechanical Cantilever-Based Biosensors", *Sensors and Actuators B*, 79: 115-126, 2001.

Roulet, et al., "Fabrication of Multilayer Systems Combining Microfluidic and Microoptical Elements for Fluorescence Detection", Journal of Microelectromechanical Systems, 10(4): 482-491, 2001.

Ryu, et al., "Precision Patterning of PDMS Thin Films: A New Fabrication Method and Its Applications", Defense University Research Initiative in Nanotechnology Program (NAVY CL 2468 ANTIC) the Nano Science and Engineering Center, no date provided.

Savran, et al., "Fabrication and Characterization of a Micromechanical Sensor for Differential Detection of Nanoscale Motions", *Journal of Micromechanical Systems*, 11(6): 703-708, 2002.

Schmid, et al., "Siloxane Polymers for High-Resolution, High-Accuracy Soft Lithography", *Macromolecules*, 33: 3042-3049, 2000.

Sparks, et al., "A Density/Specific Gravity Meter Based on Silicon Microtube Technology", *Proceedings Sensors Expo*, 171-176, 2002.

Sparks, et al., "A Microfluidic System for the Measurement of Chemical Concentration and Density", *IEEE*, 300-303, 2003.

Stern, et al., "Nanochannel Fabrication for Chemical Sensors", *J. Vac. Sci. Technol. B*. 15(6): 2887-2891, 1997.

Tamayo, et al., "Chemical Sensors and Biosensors in Liquid Environment Based on Microcantilevers with Amplified Quality Factor", *Ultramicroscopy*, 86: 167-173, 2001.

Thundat, et al., "Detection of Mercury Vapor Using Resonating Microcantilevers", *Appl. Phys. Lett*, 66(13): 1695-1697, 1995.

Tsau, et al., "Fabrication of Wafer-Level Thermocompression bonds" *Journal of Microelectromechanical Systems*, 11(6): 641-647, 2002.

Vinod, et al., "A Novel SiC on Insulator Technology Using Wafer Bonding", International Conference on Solid-State Sensor and Actuators, 653-656, 1997.

Vörös, et al., "Optical Grating Coupler Biosensors", *Biomaterials*, 23: 3699-3710, 2002.

Walsh, et al., Photoresist as a Sacrificial Layer by Dissolution in Acetone, *IEEE*, 114-117,2001.

Wego, et al., "Fluidic Microsystems Based on printed Circuit Board Technology", *J. Micromech. Microeng.* 11: 528-531, 2001.

Westberg, et al., "A CMOS-Compatible Fluid Density Sensor", *J. Micromech. Microeng*. 7: 253-255, 1997.

Westberg, et al., "A CMOS-Compatible Device for Fluid Density Measurements Fabricated by Sacrificial Aluminium Etching", *Sensors and Actuators*, 73: 243-251, 1999.

Wiegand, et al., "Wafer Bonding of Silicon Wafers Covered with Various Surface Layers", *Sensors and Actuators*, 86: 91-95, 2000.

Wolffenbuttel, R., "Low-Temperature Intermediate Au-Si Wafer Bonding: Eutectic or Silicide Bond", *Sensors and Actuators A*, 62: 680-686, 1997.

Wu, et al., "Bioassay of Prostate-Specific Antigen (PSA) Using Microcantilevers", *Nature Biotechnology*, 19: 856-860, 2001.

Enoksson, et al., "Fluid Density Sensor Based On Resonance Vibration" *Sensors and Actuators A* 46-47: 327-331, 1995.

Enoksson, et al., "Vibration Modes of a Resonant Silicon Tube Density Sensor" *Journal of Microelectromechanical Systems* 5(1): 39-44,1996.

* cited by examiner

SUSPENDED MICROCHANNEL DETECTORS

PRIORITY CLAIM

This application is a Continuation-in-Part of U.S. patent application Ser. No. 10/336,549 by Manalis et al. entitled "Measurement of Concentrations and Binding Energetics" filed on Jan. 2, 2003, which claims the benefit of Provisional Application No. 60/405,184, filed on Aug. 22, 2002.

GOVERNMENT SUPPORT

The work described herein was supported, in part, by grants from the Defense Advanced Research Projects Agency (DARPA) (MDA972-001-1-003). The United States government may have certain rights in the invention.

BACKGROUND

Conventional procedures based on two-dimensional gel electrophoresis for profiling the concentrations of specific proteins and their byproducts are time-consuming, labor-intensive, and require significant technical expertise to obtain quantitative information. One approach for circumventing these limitations is to develop the equivalent of a DNA microarray for proteins. Protein microarrays consist of various types of capture ligands that exhibit a high binding affinity toward a particular protein. Target proteins are either labeled with a fluorescent label, or additional fluorescently labeled protein is used to selectively bind to the target once it has been capture to a specific site on the array. The latter approach, often referred to as a sandwich assay, has the advantage of being extremely selective since very rarely will a target protein bind to both the capture molecule and an additional protein. This disadvantage of the sandwich assay is that there are a limited number of target proteins for which there exist two distinct binding partners. As a result, direct labeling of the target protein can be most generally applied for profiling multiple proteins from a cell lysate. However, there are two drawbacks of direct labeling: First, the efficiency of coupling fluorescent labels to low abundance proteins within a lysate is highly variable. This can often make it difficult to achieve sufficient sensitivity as well as reliability. Second, the complexity of protein structures poses significant challenges for attaching labels to specific sites while preserving the functionality of a protein. This challenge was cogently summarized by biophysicist S. P. Fordor: "Conventional detection techniques based on fluorescent tagging require that one partner of a complex is chemically modified. These modifications can subtly alter molecular interactions by changing the chemical nature of the binding interaction." Mazzoila, L. T. and Fordor, S. P. A., Biophys. J. (1995), 68:1653-1660, the entire teachings of which are incorporated herein by reference. Thus, eliminating the labeling process will improve the feasibility, speed, and utility of quantitative protein assays.

The major limitation of existing label-free detectors is that they are significantly less sensitive than fluorescence detection. The two most well known approaches are the quartz crystal microbalance (QCM) for detecting surface adsorbed mass and the surface plasmon resonance (SPR) technique for detecting refractive index changes in close proximity to a metal surface. Both methods have significant fundamental limitations concerning scalability, sensitivity to low-concentration samples, and their ability to provide quantitative information. The mass resolution of the QCM is on the order of $10^{-17}$ g/$\mu m^2$, which corresponds to about 100 proteins/$\mu m^2$ (assuming a molecular weight 100 kDa). Furthermore, the QCM sensor area is macroscopic in scale (typically a few $mm^2$), so the minimum detectable mass is on the order of several nanograms, or $10^{10}$ molecules. This detection level is not suitable for many biological assays. Fluorescence routinely resolves 1-10 molecules for a surface area less than 100 $\mu m^2$. The QCM also requires that the capture ligands be rigidly coupled to the sensor surface. This limits the efficiency of three-dimensional coatings (e.g. carboxymethyl-dextran (CMD) matrix) that enhance the effectiveness of mass sensing.

The SPR, which achieves a similar resolution as the QCM, measures changes in the refractive index that occur within a CMD layer above the sensor surface several hundred nanometers thick. Since the influence of the target molecules on the optical properties of this layer is generally unknown, SPR usually provides indirect information. This can make it difficult to quantify the amount of bound target molecules. Furthermore, attempts to reduce the sensor surface area for large-scale integration are not yet capable of reaching sensitivity levels that are comparable to commercial macroscopic instruments. This limitation is often attributed to the difficulty of matching the very narrow operating range of the integrated optics to the refractive index of typical buffer solutions using materials available for micro-fabrication.

The development of label-free detectors that are both sensitive and scalable (both down in sensor area and up in number of sensors) is in its infancy. In addition to on-going research for advancing optical methods as well as acoustical methods such as the flexural plate wave device (FPW), there are several new approaches for label-free detection that are currently being pursued. One approach for molecular detection is the transduction of surface binding events on a microcantilever into mechanical bending. The bending is not induced by the addition of mass but rather the change in surface energy resulting from specific binding of the bio-molecules. For example, it has been shown that a microcantilever stress sensor can detect DNA hybridization. In other work, it has been shown that the microcantilever stress sensor can detect prostate-specific antigen (PSA) in a background of human serum albumin and human plasminogen (Wu et al., Nature Biotech. (2001), 19:856, the entire teachings of which are incorporated herein by reference). This result suggests that the stress sensor could be a clinically relevant diagnostic technique for prostate cancer.

The advantage of using microcantilevers for label-free detection is that this technique is scalable. For example, researchers at IBM Zurich have demonstrated that eight cantilevers can be detected in parallel (Arntz, et al., Nanotechnology (2003), 14(1): 86 and Battiston, et al., Sensors and Actuators B-Chemical (2001), 77(1 and 2): 122-131, the entire teachings of which are incorporated herein by reference). However, there are three drawbacks to using the microcantilever stress sensor. First, there is not yet a viable approach for integrating the cantilevers with conventional microfluidics. Currently, the surfaces must be functionalized by manually aligning micropipettes to each cantilever before packaging the cantilevers within a macroscopic fluid cell. Second, the surface stress induced by molecular binding must occur on only one side of the cantilever in order for it to bend. This requires different surface chemistries to be developed for the top and bottom sides of the sensor. Third, it has not yet been demonstrated (or predicted) that the stress sensor has a higher resolution (in terms of minimum number of detectable molecules per area) than commercially available sensors such as the SPR. Despite these limitations, the development of the microcantilever stress sensor is still in its infancy and its full potential has yet to be realized.

Finally, resonant cantilever mass sensors, while successful for chemical sensing in gaseous environments, have received less attention for biomolecular detection in solution. This is primarily because the mass sensitivity and frequency resolution are significantly degraded by the low quality factor and large effective mass that is induced by viscous drag. While the quality factor can be enhanced by using electronic feedback known as Q-control, the mass sensitivity, in terms of frequency shift per mass loading, is not improved.

Accordingly, there remains a need for an analytical technique that is sufficiently sensitive but does not require modification of the analyte of interest.

SUMMARY OF THE INVENTION

The present invention relates to an apparatus that is a label-free detector for measuring a property of an analyte. The apparatus comprises at least one suspended beam connected to two mechanically stable supports. The suspended beam may contain one or more microfluidic channels, and each microfluidic channel has at least one chemical species that binds to or reacts with the analyte. The apparatus also comprises one or more detectors for measuring a change in the one or more beams upon binding or reaction of the analyte. In one embodiment, the suspended beam is resonating.

One disadvantage of a cantilever microfluidic channel is that the sample fluid must enter and exit the microfluidic channel through the end of the cantilever that is attached to the semiconductor wafer. Thus, a cantilever having a microfluidic channel must have a sharp bend at the free end of the cantilever where the channel doubles back on itself to exit through the attached end of the cantilever. A detector having a suspended beam connected to two mechanically stable supports with a microfluidic channel that flows through the beam is often preferable to a cantilever type beam because the microfluidic channel contains no sharp bends and thus components of the sample fluid other than the analyte are less likely to collect in the microcrofluidic channel.

In another embodiment, the apparatus of the invention for detecting an analyte or measuring a property of the analyte, comprises a device structure that has at least one suspended beam that contains one or more microfluidic channels, wherein each microfluidic channel has at least one chemical species that binds to or reacts with an analyte; and a sample fluid channel having a depth that is substantially larger than the microfluidic channel connected to the inlet of at least one of the microfluidic channel. The apparatus may also include one or more detectors for measuring a change in the beam upon binding or reacting of the analyte. In this embodiment, the suspended beam may be either a cantilever or the beam may be suspended between two mechanically stable supports. In one preferred embodiment, the apparatus is a micro-electro-mechanical system (MEMS) that has a packaging structure that covers the device region. In one embodiment, the packaging structure is sealed to the device region such that the suspended beam is in a controlled environment. This allows the device to be protected from environmental factors, such as variations in humidity, dust particles, static charge build-up, ect., that could decrease the signal to noise ratio of the device. In one embodiment the packaging structure is sealed to the device region such that the suspended beam is in a low pressure environment (i.e., an environment that is less than atmospheric pressure).

In another aspect, the invention is related to a method of fabricating a functionalized microfluidic channel having an inlet and an outlet. The method involves depositing a first channel layer on a semiconductor wafer having one or more trenches. A sacrificial layer is deposited on the first insulator layer, then a planarization technique, such as chemical-mechanical polishing, is used to remove the sacrificial layer down to the first channel layer, thereby exposing a planar surface of the first insulator layer having the sacrificial layer in the trenches. A second channel layer is deposited on the planar surface, and one or more holes are formed in the second channel layer that are connected to one or more of the trenches. The sacrificial layer, or a portion thereof, is then removed from the trenches by etching, thereby forming a microfluidic channel. The interior of the microfluidic channels is then functionalized with a capture ligand. The functionalization step may take place either before or after a packaging structure containing connections with sample fluid channels is added to the device containing the microfluidic channels. In one embodiment, a portion of the backside of the semiconductor wafer (i.e., the side of the semiconductor wafer opposite to the side on which the channel layers are deposited) is removed below the microfluidic channel thereby forming a suspended microchannel. Preferably, the portion of the semiconductor wafer below the microfluidic channel is etched back to the first channel layer. In one embodiment, the backside of the semiconductor wafer is etched simultaneously with removal of the sacrificial layer from the trenches. In one preferred embodiment, the semiconductor wafer is a silicon wafer, the first and the second channel layers are silicon nitride or silicon dioxide and the sacrificial layer is polysilicon. In this embodiment, a portion of the sacrificial layer may be doped with either a p-type or n-type dopant. Heavily doped polysilicon (e.g., a dopant concentration of about $5\times10^{19}$ $cm^{-3}$ or greater) is resistant to etching with potassium hydroxide. Thus, the sacrificial layer may be removed by etching with a potassium hydroxide and the heavily doped areas will remain in the microfluidic channel. The heavily doped polysilicon areas of the channel will be electrically conductive. Alternatively, the microfluidic channel may be made electrically conductive by having the first and the second channel layers that are made from heavily doped polysilicon.

Using the method of the invention, very thin microfluidic channels having very thin walls may be formed with the method of the invention. The sensitivity of a resonant mass detector is enhance by decreasing the thickness of the resonating beam. In addition, the method may be used to form microfluidic channels from materials that are not amenable to wafer bonding, such as silicon nitride.

In another aspect, the invention is related to a packaged a device comprising one or more suspended microfluidic channel formed in a semiconductor wafer, and a method of making the same. The method involves patterning a substrate with one or more separately addressable electrodes, wherein the electrodes can be aligned with each microfluidic channel of the device; preparing a poly(dimethyl siloxane) gasket having one or more fluid channels and one or more opening; bonding the gasket to the substrate; patterning a common electrode on the surface of the device, wherein the common electrode is formed on each microfluidic channel; and bonding the gasket to the device, wherein the fluid channels of the gasket connect with the inlets and outlets of the microfluidic channels of the device and each opening on the gasket is aligned with one or more suspended microfluidic channel.

In another embodiment, the invention involves a method of packaging a device comprising one or more suspended microfluidic channels formed in a semiconductor wafer. The method involves forming one or more fluid channel and one or more cavities in a substrate, wherein the cavities can be aligned with the microfluidic channels; patterning the cavities of the substrate with one or more separately addressable electrodes, thereby forming electrodes that can be aligned with each microfluidic channel of the device; patterning a common electrode on the surface of the device, wherein the common electrode is formed on each microfluidic channel; and bonding the substrate to the device, wherein the fluid channels of the substrate connect with the inlets and outlets of the microfluidic channels of the device and each trench of the substrate is aligned with one or more suspended microfluidic channel.

In another embodiment, the invention relates to a method of packaging a device comprising one or more suspended microfluidic channel formed in a semiconductor wafer. The method involves patterning a surface of a substrate with one or more separately addressable electrodes; forming a photoresist on the surface of the patterned substrate; irradiating the photoresist through a mask, thereby removing the photoresist from predetermined areas of the substrate; electroplating a metal in the area of the substrate where the photoresist was removed, thereby forming the walls of the one or more microfluidic channels and the walls of the one or more cavities; removing the remainder of the photoresist; patterning a common electrode on a surface of the device having an inlet and an outlet for each of the microfluidic channels; and bonding the electroplated metal to the common electrode, wherein the fluid channels formed by the electroplated metal walls connect with the inlets and outlets of the microfluidic channels of the device and each cavity formed by the electroplated metal walls is aligned with one or more suspended microfluidic channel.

The packaging methods of the invention allow for the microfluidic channels to be in a controlled environment and allow the microfluidic channels of the device to be connected to larger sample fluid channels. In addition, the packaging methods integrate drive electrodes and detectors that provide the electrostatic driving force that causes each microfluidic channel to resonate. Thus, the packaging methods of the invention allow hundreds of devices to be produced from a single wafer.

BRIEF DESCRIPTION OF THE DRAWING

The invention is described with reference to a particular embodiment shown in the figures. The embodiment in the figures is shown by way of example and is not meant to be limiting in any way.

DETAILED DESCRIPTION

Figure 1:
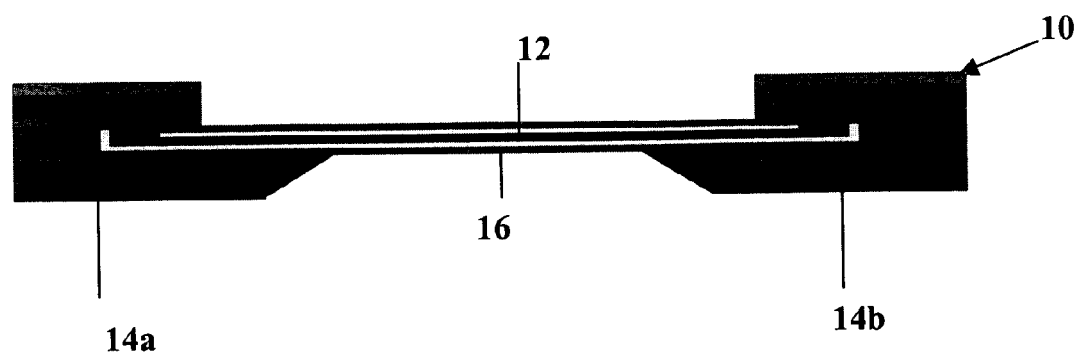
FIG. 1 is a schematic representation of one embodiment of an apparatus of the invention that has a suspended beam connected to two mechanically stable supports.

The apparatus of the invention is a new method of detecting biomolecules whereby a suspended microfluidic channel is used to capture specific target molecules onto the interior channel walls. The amount of bound target molecules is determined by measuring the change in resonant frequency during the adsorption. There are three key properties that enable this method of detection: First, the mass density of biomolecules is different than the density of the water. For example, proteins have a mass density in the range of 1.3-1.4 $g/cm^3$. Thus, the net mass of the fluid-filled resonator depends on the total number of biomolecules that are contained within the resonator. Second, the difference in energy loss of the resonator (quality factor, Q) between an air-filled and fluid-filled microchannel is insignificant. As a result, the mass sensitivity as well as the frequency detection resolution are not degraded by viscous drag of the solution. This is not the case for resonating detectors where the capture ligands are on the external portion of beam that is immersed in a solution containing the analyte. Resonating detectors of this type have a low quality factor due to viscous drag of the solution. Third, the surface to volume ratio of the microchannel must be sufficiently large such that number of surface-bound molecules is generally much large than the number of molecules contained within the microchannel volume. Thus, the binding of target biomolecules to the microchannel walls can be monitored in real-time.

The suspended microfluidic channel detector enables the extraordinary high mass resolution associated with a resonator in vacuum while preserving the highly selective biomolecular recognition that occurs only within the aqueous environment. In other words, the target molecules (or analytes) that bind to the capture ligands within the oscillating microchannel are not aware that the exterior of the channel is vacuum, or a gas. Suspended microfluidic channels are also scalable and allow analytes to be detected in a low volume of sample fluid (~10 pL per detector)

Decreasing the channel thickness and the thickness of the walls of the channel, as well as, increasing the number of capture ligands bound to the interior of the channel should increase the resolution. Integrating microfluidic channel detectors with conventional microfluidics will increase the utility of such detectors and allow multiple detectors to be fabricated on one semiconductor wafer. It has been predicted that a suspended microchannel with a surface area of $10^4$ $\mu m^2$ should be capable of resolving ~1 protein/$\mu m^2$ (assuming a 100 kD protein mass).

A resonant mass sensor with internal surface area A can be modeled as a harmonic oscillator with an effective mass m and resonance frequency f. The relative frequency shift $\Delta f/f$ resulting from a small surface mass loading $\Delta\sigma = \Delta m/A$ is given to first order by equation (1):

$$\frac{\Delta f}{f} = -\frac{1}{2}\left(\frac{A}{m}\right) \cdot \Delta\sigma \qquad (1)$$

Equation (1) shows that for a given detectable frequency shift $\Delta f$ and a resonance frequency f, the smallest detectable surface mass loading is fully determined by the ratio of surface area to total mass. This ratio can be improved by reducing the thickness of the fluid layer as well as that of the channel walls.

Figure 2:
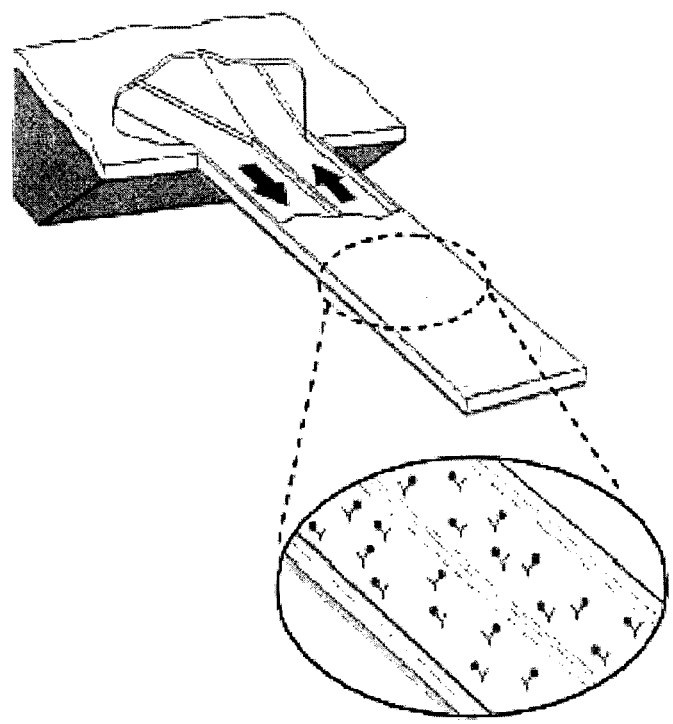
FIG. 2 is a schematic representation of one embodiment of an apparatus of the invention that has a cantilever suspended beam.

In one embodiment, the apparatus 10 (see FIG. 1) of the invention for detecting an analyte or measuring a property of an analyte, comprises at least one suspended beam 12 connected to two mechanically stable supports 14a and 14b, wherein the beam contains one or more microfluidic channels 16; and one or more detectors (not shown). In an alternative embodiment, the beam may be a cantilever (see FIG. 2). A microfluidic channel is a channel that has an inlet and an outlet and a depth and a height in the range of between about 50 nm and about 2000 nm. In one embodiment, the microfluidic channel has a depth in the range of between about 100 nm and about 1200 nm. Each microfluidic channel has at least one chemical species that binds to or reacts with the analyte. The one or more detectors measures a change in the resonance frequency of the one or more beams upon binding or reaction of the analyte. Detection is accomplished by transducing the mass of adsorbed analyte molecules into changes in mechanical resonant frequency.

In one embodiment, the chemical species is a capture ligand that binds to the analyte. A capture ligand is a molecule that has a high capacity of molecular recognition for another molecule or complex and a high capacity to specifically bind to the molecule or complex. Unless specified as a covalent bond, the term "bind" or "bound" includes both covalent and non-covalent associations. "Specific binding," as used herein, is when a capture ligand binds one or more other molecule or complex (i.e., the target), with specificity sufficient to differentiate between the molecule or complex and other components or contaminants of a sample. In one embodiment, the dissociation constant of the capture ligand for the target less than about $1 \times 10^{-6}$ M. In another embodiment, the capture ligand may be one member of a molecular recognition system. Molecular recognition systems for use in the invention are conventional and are not described here in detail. Techniques for preparing and utilizing such systems are well known in the art and are exemplified in the publication of Tijssen, P., "Laboratory Techniques in Biochemistry and Molecular Biology Practice and Theories of Enzyme Immunoassays" (1988), eds. Burdon and Knippenberg, New York:Elsevier, the entire teachings of which are incorporated herein. Preferred molecular recognition systems include an antigen/antibody, an antigen/antibody fragment, an avidin/biotin, a streptavidin/biotin, a protein A/$I_g$ or a lectin/carbohydrate. Either member of the molecular recognition system may be a capture ligand. The other member of the molecular recognition system will be the target. In one embodiment, the target of a capture ligand is an antigen on the surface of a cell, such as a cell surface receptor, an integrin, a transmembrane protein, and ion channel or a membrane transport protein.

Other capture ligands include nucleic acids (e.g., DNA and RNA) or modified nucleic acids (e.g., DNA or RNA with modified bases or modified backbones). In addition, the nucleic acids may be single stranded or double stranded. Nucleic acids and modified nucleic acids generally will bind a target nucleic acid that has a sequence that has at least three, preferably eight, consecutive nucleic acids that are complementary to the sequence of the capture ligand.

The term "nucleic acids," or "oligonucleotides," as used herein, refers to a polymer of nucleotides. Typically, a nucleic acid comprises at least three nucleotides. The polymer may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available (e.g. see, www.trilinkbiotech.com, www.appliedbiosystems.com, www.biogenex.com or www.syngendna.com).

The capture ligand may also be a nucleic acid ligand, such as an aptamers. As used herein, "nucleic acid ligand" is a non-naturally occurring nucleic acid that binds selectively to a target. The nucleic acid that forms the nucleic acid ligand may be composed of naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In one embodiment, nucleotides or modified nucleotides of the nucleic acid ligand can be replaced with a hydrocarbon linker or a polyether linker provided that the binding affinity and selectivity of the nucleic acid ligand is not substantially reduced by the substitution (e.g., the dissociation constant of the nucleic acid ligand for the target should not be greater than about $1 \times 10^{-6}$ M). The target molecule of a nucleic acid ligand is a three dimensional chemical structure that binds to the nucleic acid ligand. However, when the target is another nucleic acid, the nucleic acid ligand is not simply a linear complementary sequence of a nucleic acid target but may include regions that bind via complementary Watson-Crick base pairing interrupted by other structures such as hairpin loops). Targets of nucleic acid ligands include small molecules, peptide, polypeptide, carbohydrate and nucleic acid molecules.

Another type of capture ligand is a protein nucleic acid (PNA). A PNA has a peptide backbone in which a natural or non-natural nucleic acid base is attached to each amino acid residue. A PNA can recognize a nucleic acids that have a complementary sequence of at least three consecutive bases, preferably eight consecutive bases, to the sequence of the PNA.

In one embodiment, the capture ligand is bound to the interior surface of the microfluidic channel. One method of binding the capture ligand to the interior surface of the microfluidic channel is to bind a linker to the interior surface of the microfluidic channel, then bind the capture ligand to the linker. The linker must have one or more groups that will bind to the surface of the microfluidic channel and one or more groups that will bind to the capture ligand (such as a primary or secondary amine, —OH, —SH, or a halo). For example, when the interior surface of the microfluidic channel is silicon nitride or silicon dioxide, one method of binding the capture ligand to the interior surface of the microfluidic channel is to contact the surface of the microfluidic channel with a silane linker. A silane linker is a molecule that has at least one silyl group that can bind to a silicon dioxide or silicon nitride surface and at least one other group that can bind to the capture ligand. The capture ligand is then reacted with the free functional group, thereby binding the capture ligand to the inner surface of the microfluidic channel. In one embodiment, the capture ligand can be represented by the following structural formula:

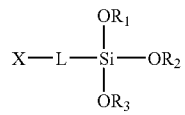

wherein:
$R_1$, $R_2$ and $R_3$ are each, independently, —H, an alkyl, or an arylalkyl;
L is an alkylene, a cycloalkylene, a heteroalkylene, a heterocycloalkylene, a sugar residue, or an arylalkylene; and
X is an —NHR, —OH, —SH, or a halo, wherein R is —H, an alkyl, an arylalkyl, or an aryl.

In another embodiment, the interior surface of the microfluidic channel is gold, silver, copper, cadmium, zinc, palladium, platinum, mercury, lead, iron, chromium, manganese, tungsten, or any alloys thereof, and the linker contains a thiol group which can bind to these surfaces and another group that can bind to the capture ligand.

When the interior surface of the microfluidic channel is an oxide, such as silicon dioxide, the linker may have a carboxylic acid group that will bind to the oxide surface and another group that can bind to the capture ligand.

When the interior surface of the microfluidic channel is platinum, palladium or any alloy thereof, the linker may have a nitrile or an isonitrile that can bind to these surfaces and another group that can bind to the capture ligand.

When the interior surface of the microfluidic channel is copper, the linker may have a hydroxamic acid that can bind to this surface and another group that can bind to the capture ligand.

An alternative way of binding the capture ligand to the interior surface of the microfluidic channels is to select a capture ligand that has a group that will bind to the interior surface of the microfluidic channel or to modify the capture ligand itself so it contains a group that will bind to the interior surface of the microfluidic channel. For example, the capture ligand may be modified to contain a thiol group that will bind to microfluidic channels that have interior surfaces of gold, silver, copper, cadmium, zinc, palladium, platinum, mercury, lead, iron, chromium, manganese, tungsten, or any alloys thereof.

The sensitivity of the apparatus for detecting a target is improved the more target molecules that are bound in the microfluidic channel. Thus, increasing the number of capture ligand in the microfluidic channel can increase the sensitivity of the apparatus. One method of increasing the number of capture ligands that are in the microfluidic channel is to increase the surface area by roughening the interior surface of the channel.

In another embodiment, the number of capture ligands in the microfluidic channel is increased by putting a porous gel plug in the channel that has capture ligands bound to the gel. Typically, the gel is prepared by polymerizing monomer units. The capture ligand may be attached to a monomer unit and added to the prepolymer mixture. When the prepolymer mixture is polymerized the capture ligand will be bound directly to the gel. A method of binding nucleic acid capture ligands to a gel is described in U.S. Pat. No. 6,180,770, the entire teachings of which are incorporated by reference. Alternatively, when the capture ligand is larger than the pores of the gel, the capture ligand may be added to the prepolymer mixture. When the prepolymer mixture is polymerized to form a gel, the capture ligands are trapped within the pores of the gel. In one embodiment, the polymerization reaction may be initiated by radiation, such as ultraviolet light. In this embodiment, it is desirable that the walls of the microfluidic channel are made of a transparent or translucent material, such as silicon nitride, so that the prepolymer mixture can be injected into the microfluidic channel under pressure and then polymerized by directing radiation onto a section of the beam where the gel is to be polymerized.

Figure 3:
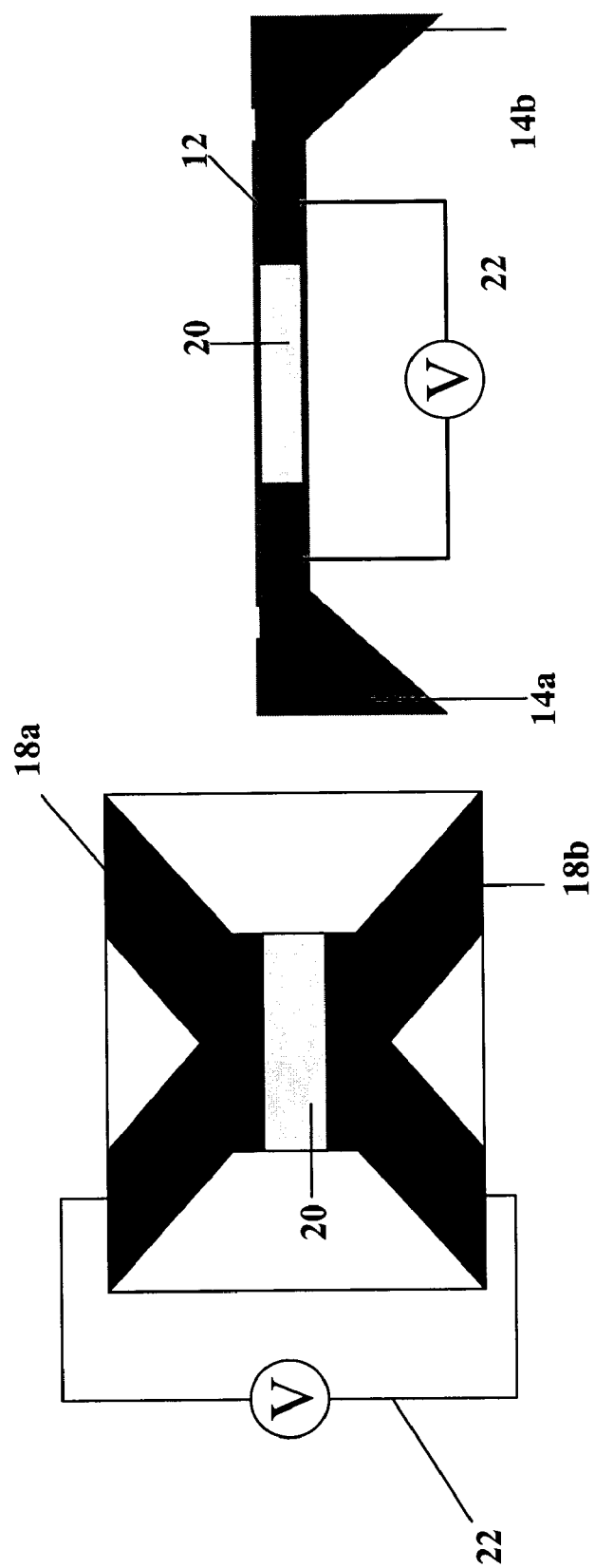
FIG. 3 is a schematic representation of a suspended beam having two microfluidic channels that converge within the beam at a point that is plugged by a gel then diverge.

One advantageous arrangement for the microfluidic channels is a beam 12 that has two microfluidic channels 18a and 18b that meet in a region containing a polymerized gel 20 and then separate downstream from the gel (see FIG. 3). In this embodiment, the analyte can be transported into the gel via pressure from the fluid flow. Alternatively, when the analyte is charged, the analyte can be transported into the gel via electrophoresis 22.

In one embodiment, the beams of the apparatus of the invention are resonating and the detector measures changes in resonance frequency of the beam. Typically, the resonance of each beam is driven by a pair of electrodes. In one embodiment, the surface of the beams may be patterned with a metal that is attached to a power source and serves as one member of the electrode pair. The other member of the electrode pair is suspended above the surface of the beam. When there is more than one beam in the apparatus, the metal electrode patterned on the beams may be connected such that the electrode is common to all beams. The electrodes suspended above each beam, however, are separately addressable. Typically, the electrodes are a metal such as gold, nickel, platinum, aluminum, copper, antimony, tin, indium, chromium, titanium, and alloys thereof. In a preferred embodiment, electrodes are gold.

In one embodiment, the beams are not patterned with a metal electrode. Instead, the solution in the microfluidic channel is an electrolyte solution that is attached to a power source. The electrolytic solution in the microfluidic channels acts as an electrode and, if each microfluidic channel is connected to the microfluidic channels in other beams of the apparatus, the electrolyte solution can act as a common electrode for all the beams. In this embodiment, there is a separately addressable electrode suspended above each beam.

In an alternative embodiment, the detector measures changes in surface stress of the beam. In one embodiment, changes in surface stress may be caused by steric stress caused by analyte molecules packing closely as they bind to the capture ligands in the microfluidic channel. In this embodiment, a substantially higher concentration of a capture ligand is bound on one side of the microfluidic channel than on the opposite side of the microfluidic channel. When the capture ligand binds to an analyte, the difference in surface stress between the two sides causes the channel to bend. In this embodiment, the detector measures the deformation of the beam.

In another embodiment, surface stress may be caused by differential expansion of the materials that make up the beam. In this embodiment, one of the outer surfaces of the beam is coated with a thin film whose thermal expansion coefficient is different from that of the channel. A capture ligand is contained inside the channel. When the capture ligand binds to an analyte, heat is released or absorbed, and the resulting change in temperature causes the beam to bend by means of a bimorph action. In this embodiment, the detector measures the deformation of the beam.

In another embodiment, the one or more detectors of the apparatus of the invention are one or more capacitors. Capacitive sensors can measure displacement as a change in the capacitance of a plane capacitor. In one embodiment, the drive electrodes are also used as a capacitive detectors. Capacitor sensors where the cantilever is one of the two capacitor plates have been developed by Blanc, et al., *J. Vac. Sci. Technolo. B* 14:901 (1996), the entire teachings of which are incorporated herein by reference.

Alternatively, the detector may be an optical lever, in which a laser beam is reflected from the apex of the beam, or a laser vibrometer, which utilizes a laser to illuminate the beam and measures the frequency response by means of Doppler shifts (see J. Yang, et al., "Mechanical behavior of ultrathin microcantilevers," *Sensors and Actuators* (2000), 82:102-107, the entire teachings of which are incorporated herein by reference).

Alternatively, the detector may be a piezoresistive or piezoelectric. In this embodiment the beam is made of a piezoresistive material which changes its electrical conductivity when it is strained.

The signal to noise ratio of the apparatus can be improved by enclosing the beam of the apparatus in a protected environment such that the beam is protected from changes in humidity, dust accumulation, and other factors that may effect the resonance frequency of the beam. In addition, since the quality factor is decreased by viscous drag on the beam from the environment in which the beam is suspended, it is desirable to have the beam suspended in a low pressure environment to improve the sensitivity of detection.

In one embodiment of the apparatus of the invention, comprises a device structure having at least one suspended beam that contains one or more microfluidic channels, wherein each microfluidic channel has at least one chemical species that binds to or reacts with the analyte; a sample fluid channel connected to the inlet of at least one of the microfluid channel, wherein the sample fluid channel has a depth that is substantially larger than the microfluidic channel; and one or more detectors for measuring a change in the one or more suspended beams upon binding or reaction of the analyte. This embodiment of the apparatus of the invention is a micro-electro-mechanical system (MEMS). In a preferred embodiment, the MEMS of the invention has a packaging structure that covers the device region and provides connections between the sample fluid channels and the microfluidic channels of the device. In addition the packaging structure can be constructed to provide a low pressure environment in which the beam is suspended.

Typically, each of the microfluidic channels has a depth in the range of between about 100 nm and about 1000 nm, and each of the sample fluid channels has a depth in the range of between about 10 µm and 100 µm.

The detector of the apparatus may measure changes in the frequency of the beam upon binding or reaction of an analyte or it may measure deformation of the beam upon binding or reaction of the analyte. When the apparatus has a resonating beam, the resonance of each beam is driven by a pair of drive electrodes as discussed above. In one embodiment, one of the electrodes of the electrode pair is common to all the beams and the other electrode of the electrode pair is suspended above the beam and is separately addressable for each beam. Preferably, the packaging structure includes the separately addressable electrodes.

Figure 4:
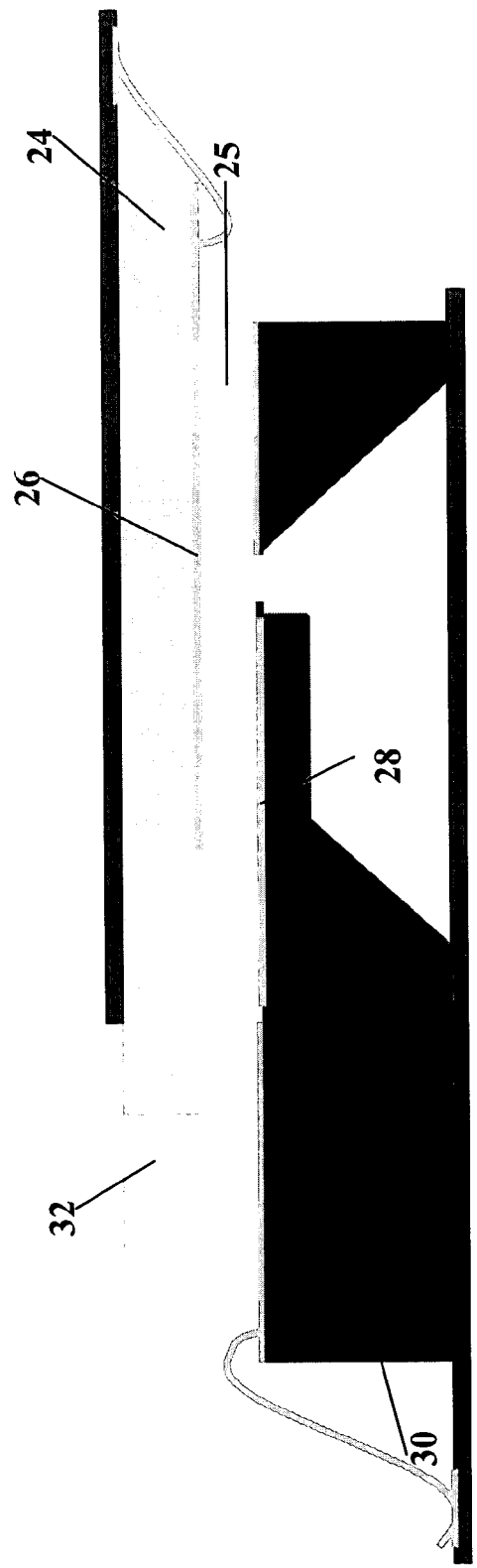
FIG. 4 is a schematic representation of one embodiment of an apparatus of the invention that is packaged using a polydimethyl siloxane gasket.

In one embodiment, the substrate is bound to the MEMS via a polydimethylsiloxane gasket. In this embodiment, the substrate can be made of glass, a ceramic, a plastics, a circuit board, and a silicon chip (with or without additional circuitry). For example (see FIG. 4), the connection between the microfluidic channels and the sample fluid channels are patterned in a polydimethylsiloxane gasket 25 (see Duffy, Anal. Chem. (1998), 70:4974, the entire teachings of which are incorporated herein by reference). The gasket is then bonded to a substrate 24 that has been patterned with the separately addressable electrodes 26 that will be suspended above each beam once the packaging structure is bound to the device. It is desirable to heat the substrate and the gasket after plasma-bonding as it generally improves adhesion between the gasket and the substrate. The surface of the device can be coated with a metal which forms the common electrode 28 or can be left uncoated when an electrolyte solution in the microfluidic channels forms the common electrode. Then the gasket is clamped to the device 30 and/or plasma-bonded to the device. Holes 32 may be etched or drilled in the substrate through which the sample fluids may be added to the device. The common electrode and the separately addressable electrodes may be used as capacitive detectors. Alternatively, the apparatus may have an optical lever detector in which a laser beam is aligned with a resonating section of the beam such that it reflects off the beam. The position of the reflected laser beam is then detected by a detector and the position of the reflected beam is transduced into information about the resonance frequency of the beam. When the apparatus has more than one beam, one laser is aligned with each beam.

Figure 5:
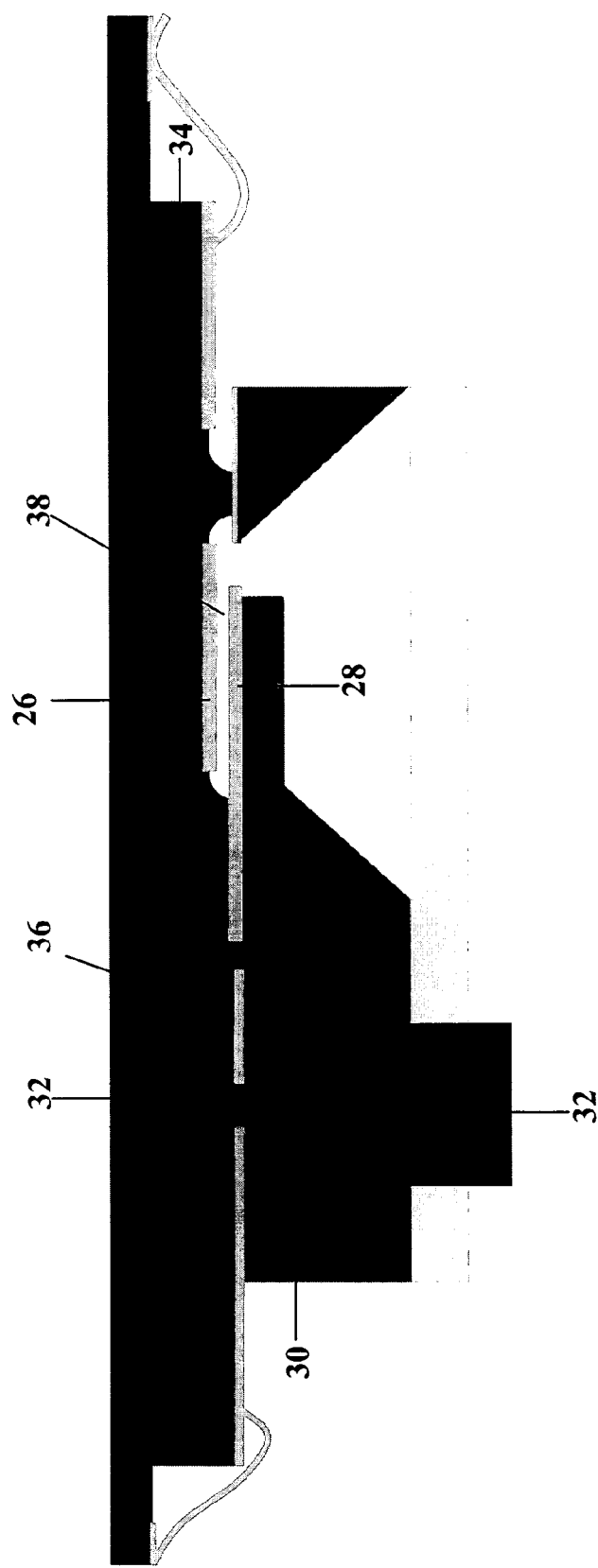
FIG. 5 is a schematic representation of one embodiment of an apparatus of the invention that has a substrate joined directly to the device by anodic bonding.

In another embodiment (see FIG. 5), the packaging structure is a glass or a silicon chip 34 substrate that has cavities 38 for the each beam and the connections between the sample fluid channels 36 and the microfluidic channels etched into the substrate. The separately addressable electrodes 26 are recessed in the cavity of the substrate that will be aligned above each beam. The surface of the device can be coated with a metal which forms the common electrode 28 or can be left uncoated when an electrolyte solution in the microfluidic channels forms the common electrode. Finally, the substrate is joined to the device 30 by anodic bonding such that the separately addressable electrodes are aligned above the beam and the sample fluid channels connect with the microfluidic channels. Holes 32 for introduction of the sample fluid may be drilled or etched into the substrate or may be etched through the device. The common electrode and the separately addressable electrodes may be used as capacitive detectors. Alternatively, the apparatus may have an optical lever detector in which a laser beam is aligned with a resonating section of the beam such that it reflects off the beam. The position of the reflected laser beam is then detected by a detector and the position of the reflected beam is transduced into information about the resonance frequency of the beam. When the apparatus has more than one beam, one laser is aligned with each beam.

Figure 6:
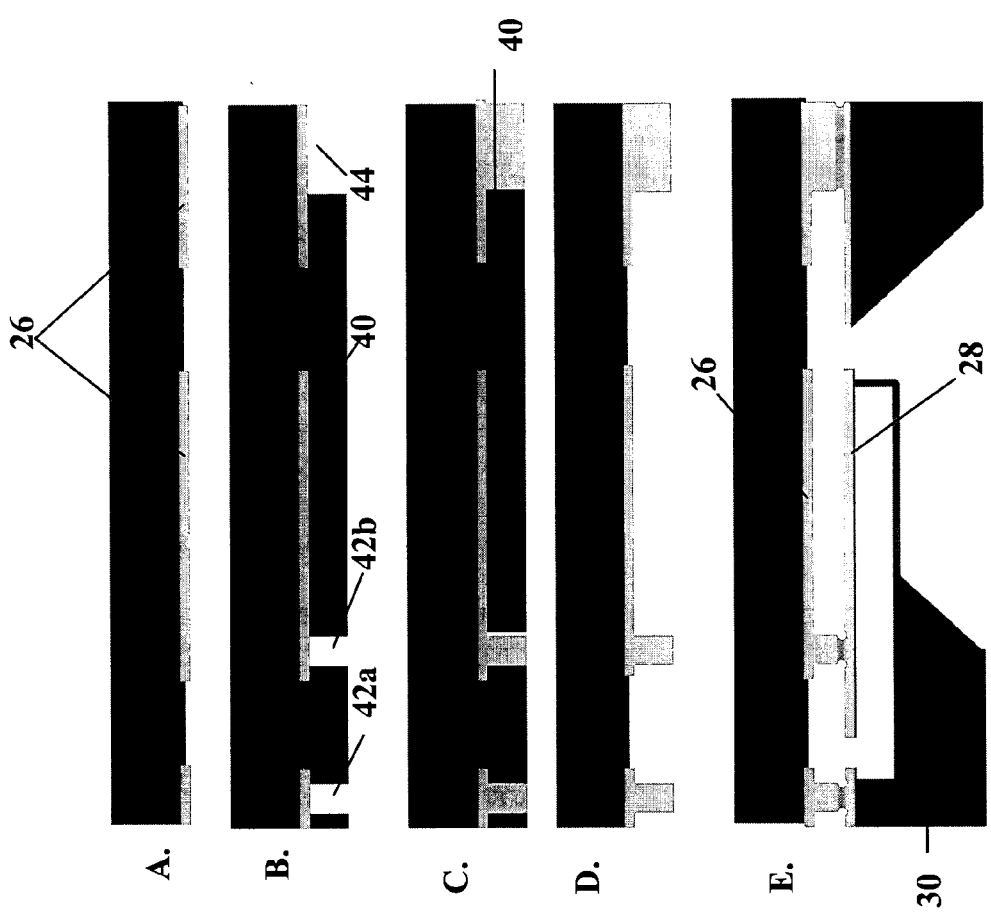
FIGS. 6A-6E are a schematic representation of a manufacturing process of one embodiment of an apparatus of the invention that has a packaging structure with a flip-chip configuration.
FIG. 6F is a schematic representation of the packaged apparatus.
Figure 6:
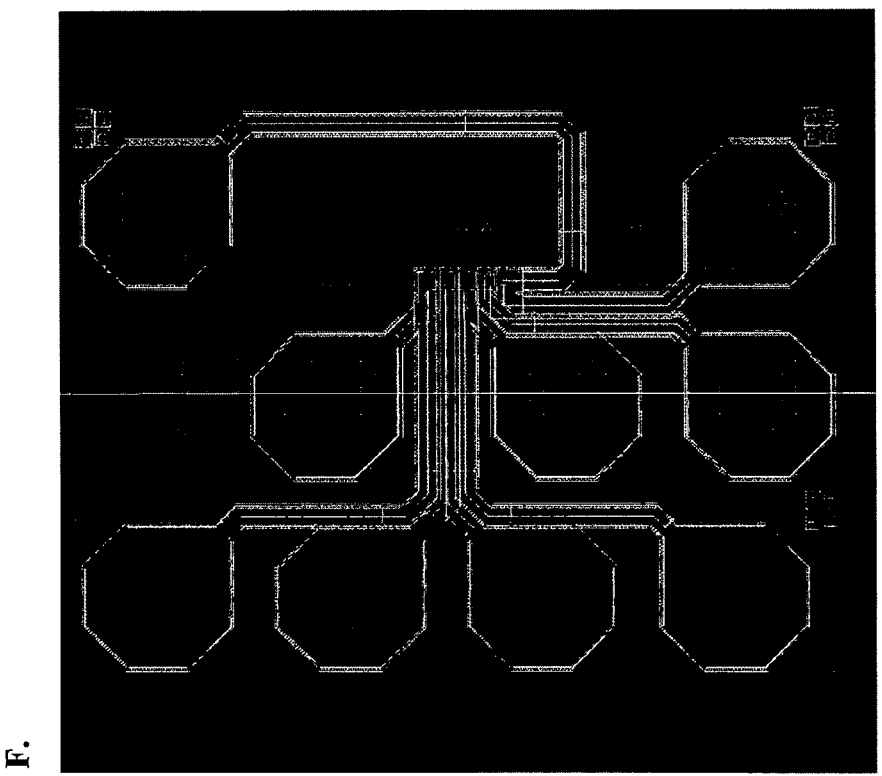

In another embodiment, the substrate is patterned with the separately addressable electrodes 26 (FIG. 6A) and a photoresist layer 40 is added to the surface of the substrate that has the patterned electrodes (FIG. 6B). The photoresist layer is irradiated through a mask, then removed from areas that will form the walls of the connection between the sample fluid and the microfluidic channel 42a and 42b and areas that will define the walls of the cavity 44 in which the beam will be suspended. A metal, such as gold, nickel, platinum, aluminum, copper, antimony, tin, indium, chromium, titanium, and alloys thereof, is then added to the open areas in the photoresist (FIG. 6C). Then the photoresist is removed leaving the metal walls that form the walls of the connection between the sample fluid and the microfluidic channel and areas that will define the walls of a cavity in which the beam will be suspended (FIG. 6D). The surface of the device can be coated with a metal which forms the common electrode 28 or can be left uncoated when an electrolyte solution in the microfluidic channels forms the common electrode. Finally, the substrate is joined to the device 30 by, for example, soldering the metal walls to the common electrode on the surface of the device, such that the separately addressable electrodes are aligned above the beam and the sample fluid channels connect with the microfluidic channels (FIG. 6E). Holes for introduction of the sample fluid may be drilled or etched into the substrate or may be etched through the device (not shown). The common electrode and the separately addressable electrodes may be used as capacitive detectors. Alternatively, the apparatus may have an optical lever detector in which a laser beam is aligned with a resonating section of the beam such that it reflects off the beam. The position of the reflected laser beam is then detected by a detector and the position of the reflected beam is transduced into information about the resonance frequency of the beam. When the apparatus has more than one beam, one laser is aligned with each beam.

Figure 7:
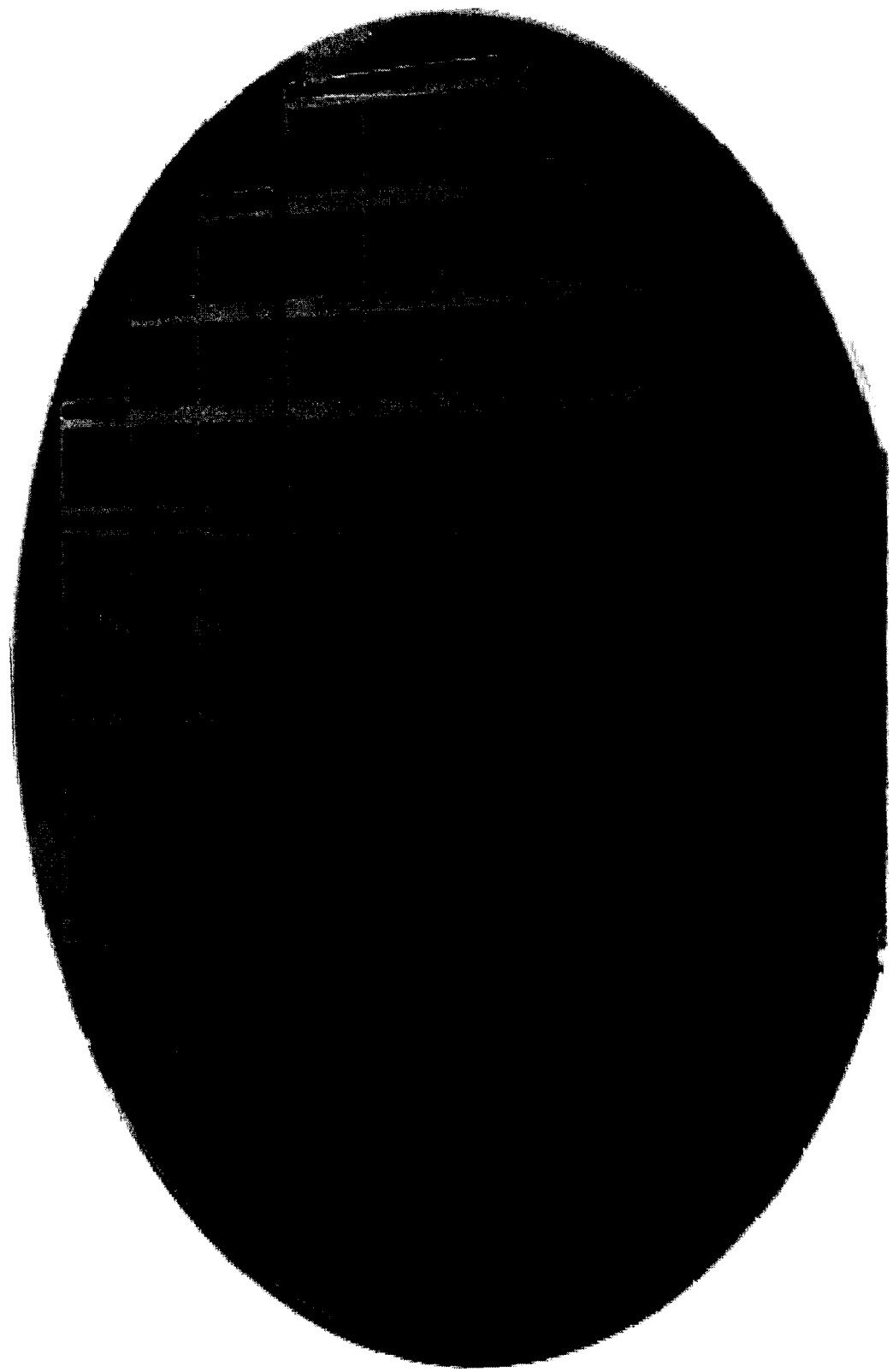
FIG. 7 shows multiple devices fabricated on one silicon wafer.

Until now microfluidic channel detectors have not yet been integrated with conventional microfluidics. Decreasing the channel thickness and the thickness of the walls of the channel, as well as, increasing the number of capture ligands bound to the interior of the channel should increase the resolution. While integrating microfluidic channel detectors with conventional microfluidics will increase the utility of such detectors and allow multiple detectors to be fabricated on one semiconductor wafer (FIG. 7).

Figure 8:
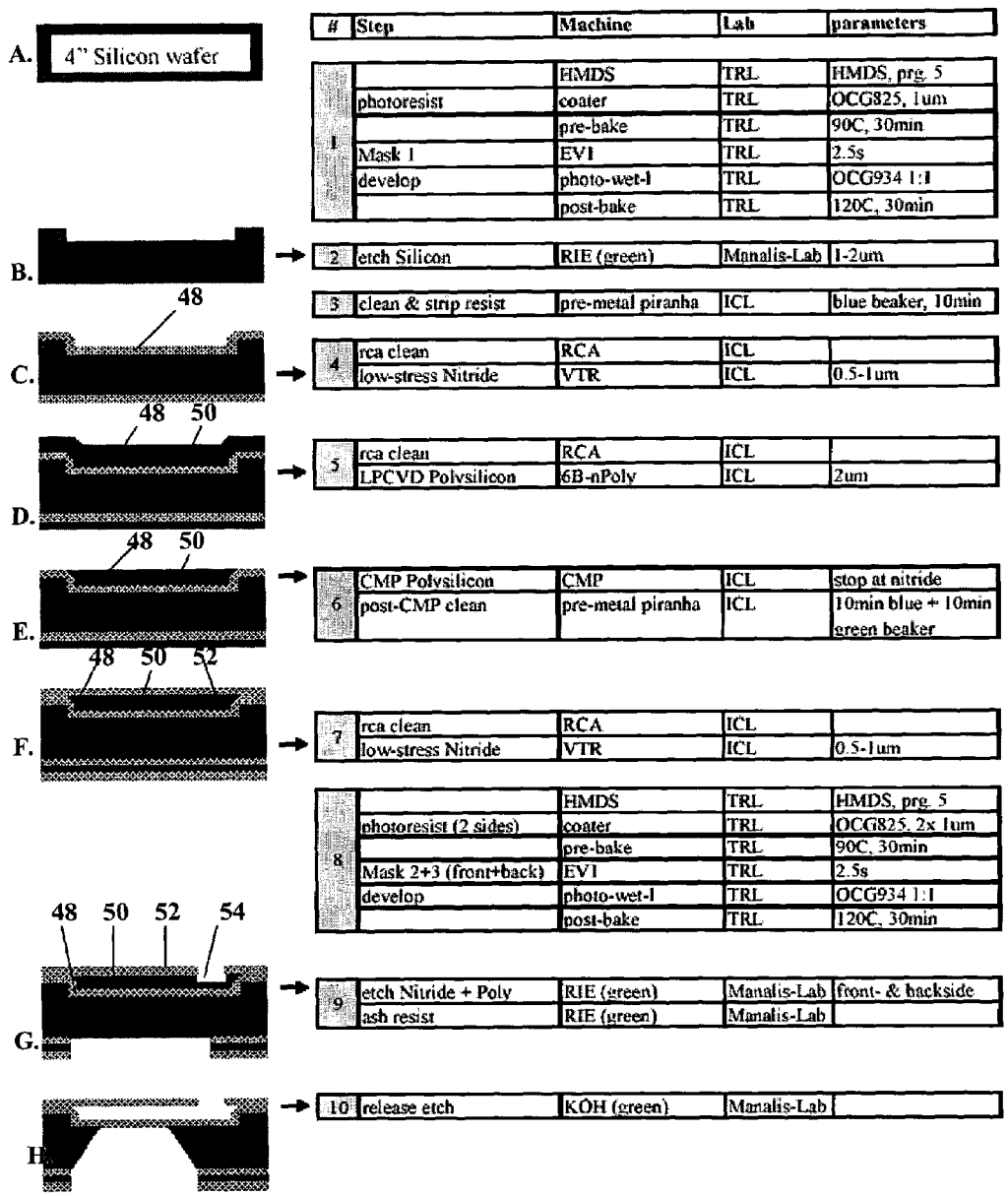
FIGS. 8A-8H are a schematic representation of one embodiment of the method of the invention for fabricating microfluidic channels.

The microfluidic channels of the invention can be fabricated by depositing a first layer 48 of a material that will make up one side of the microfluidic channel wall on a semiconductor wafer 46 having one or more trenches (FIGS. 8A, 8B and 8C). In one embodiment, the semiconductor wafer is a silicon wafer and the channel wall material is silicon nitride or silicon dioxide. A sacrificial layer 50, such as a polysilicon layer, is then deposited on the first insulator layer (FIG. 8D). Then the sacrificial layer is removed via a planarization technique, such as chemical-mechanical planarization, down to the first channel layer 48, thereby exposing a planar surface of the first channel layer having the sacrificial layer in the trenches (FIG. 8E). A second channel layer 52, such as a silicon nitride layer or a silicon dioxide layer, is deposited on the planar surface forming the other side of the microfluidic channel (FIG. 8F). Then one or more holes 54 are etched in the second channel layer that connected to one or more of the trenches (FIG. 8G). The sacrificial layer is removed from the trenches by etching, thereby forming a microfluidic channel (FIG. 8H). When the sacrificial layer is polysilicon, it can be etched by treating it with a solution of potassium hydroxide. A portion of the backside of the semiconductor wafer is removed below the microfluidic channel, for example via etching, thereby forming a suspended beam containing the microfluidic channel (FIG. 8H). This step may be done simultaneously with etching away the sacrificial layer to form the microfluidic channel. The interior of the microfluidic channels can then be functionalized as described above either before or after the device is bound to a packaging structure.

In one embodiment, it is desirable that the microfluidic channel is conductive. One method of forming a conductive microfluidic channel is to dope a portion of the polysilicon sacrificial layer with a p-type and/or an n-type dopant. Since heavily doped polysilicon (e.g., polysilicon having a dopant concentration of $5 \times 10^{19}$ cm$^{-3}$) is resistant to etching with potassium hydroxide, when the sacrificial layer is removed by etching with a potassium hydroxide solution, the doped portion of the polysilicon layer will remain in the microfluidic channel. Another method of forming a conductive microfluidic channel is to form the first and/or the second channel walls from doped polysilicon.

The method of the invention allows microfluidic channels to be formed that have a depth in the range of between about 50 nm and about 2000 nm. In one embodiment the depth of the microfluidic channels in the range of between about 100 nm and about 1000 nm. In addition, microfluidic channels can be fabricated that have very thin wall with the method of the invention. For example, microfluidic channels can be fabricated that have a wall thickness in the range of between about 100 nm and about 1200 nm. Thus, the method of the invention is advantageous since suspended beam detectors are more sensitive the thinner the microfluidic channels and the walls of the microfluidic channels.

These and other aspects of the present invention will be further appreciated upon consideration of the following Examples, which are intended to illustrate certain particular embodiments of the invention but are not intended to limit its scope, as defined by the claims.

EXAMPLES

As described above, suspended microchannels for molecular detection must be sufficiently thin, and additionally they must be configured for continuous fluidic delivery for real-time measurements. To address both of these requirements, we combined a polysilicon Damascene process, sacrificial layer etching in hot potassium hydroxide, and bulk micromachining to fabricate suspended microchannels with a wall thickness of 800 nm and a fluid layer thickness of 1.2 μm. First, we etched microfluidic trenches in a standard <100> silicon wafer using photolithography and reactive ion etching (RIE). The wafer was subsequently coated with 800 nm low-stress low-pressure chemical vapor deposited silicon nitride and followed by a 1.5 μm layer of polysilicon. The polysilicon layer was planarized with chemical mechanical polishing (CMP). The CMP process was timed to stop as soon as it reaches the silicon nitride layer so that the trenches remain filled with polysilicon. After the CMP, a second layer of low-stress silicon nitride with the same thickness as the first layer was deposited. This layer closed the microfluidic channels, which were filled with polysilicon. Again, standard photolithography and RIE was used to make an opening in the silicon nitride layer which provided access ports to the polysilicon filled microfluidic channel and to remove a portion of the backside of the wafer up to the silicon nitride layer in order to form the suspended channel. The wafer backside was also patterned in the same step to define the locations of through-holes under the suspended sections of the channel. Finally, the sacrificial polysilicon and the wafer through-holes was etched in a 6M aqueous potassium hydroxide solution at 80° C. We found that at this temperature, diffusion did not severely limit the etch rate for the sacrificial layer. We were able to completely release channels up to 1 mm in less than 20 h with a yield of 80%. (See FIG. 8 for a flow diagram of this method).

Figure 9A:
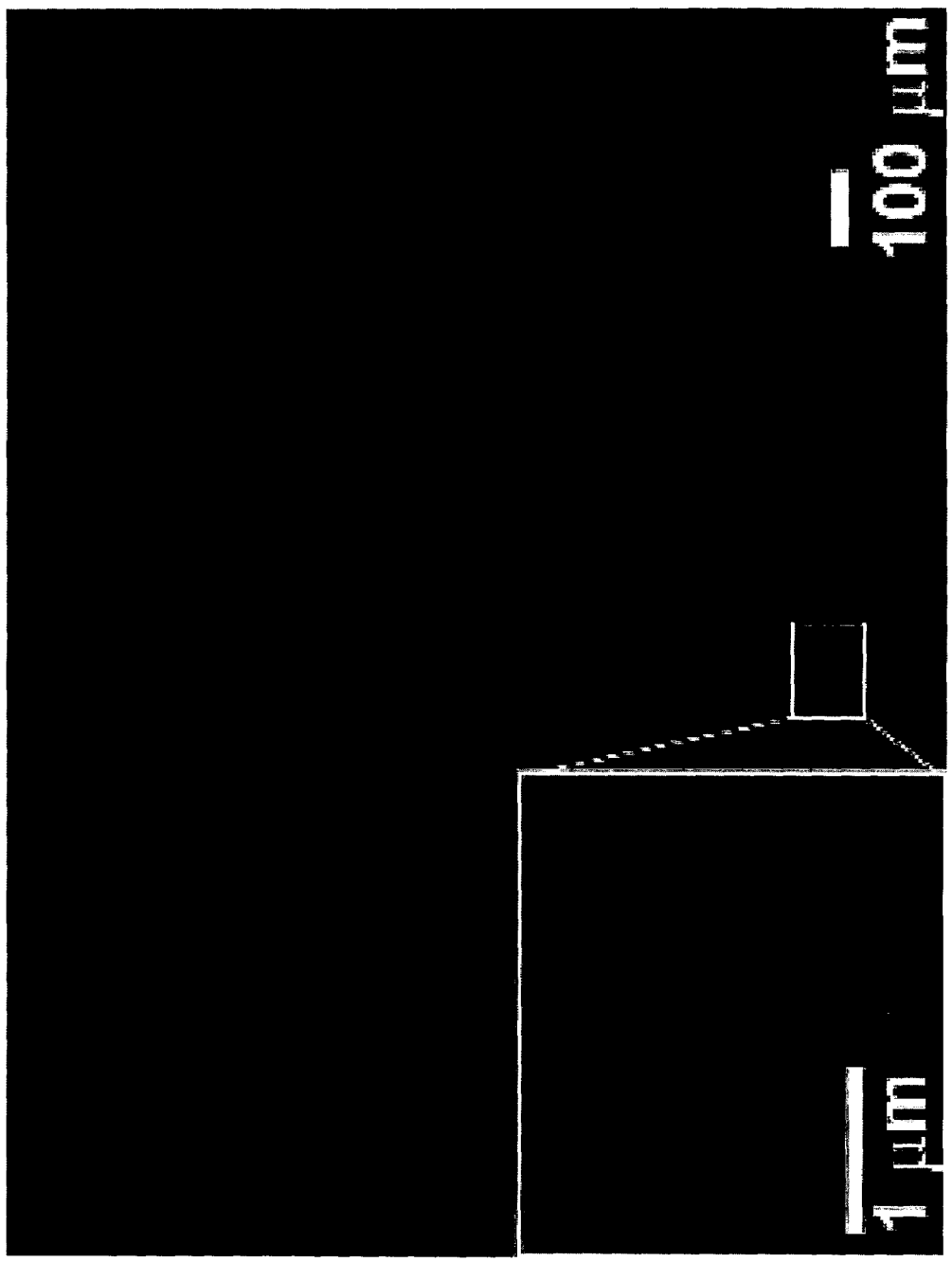
FIG. 9A is an electron micrograph of three suspended microfluidic channels.
Figure 9B:
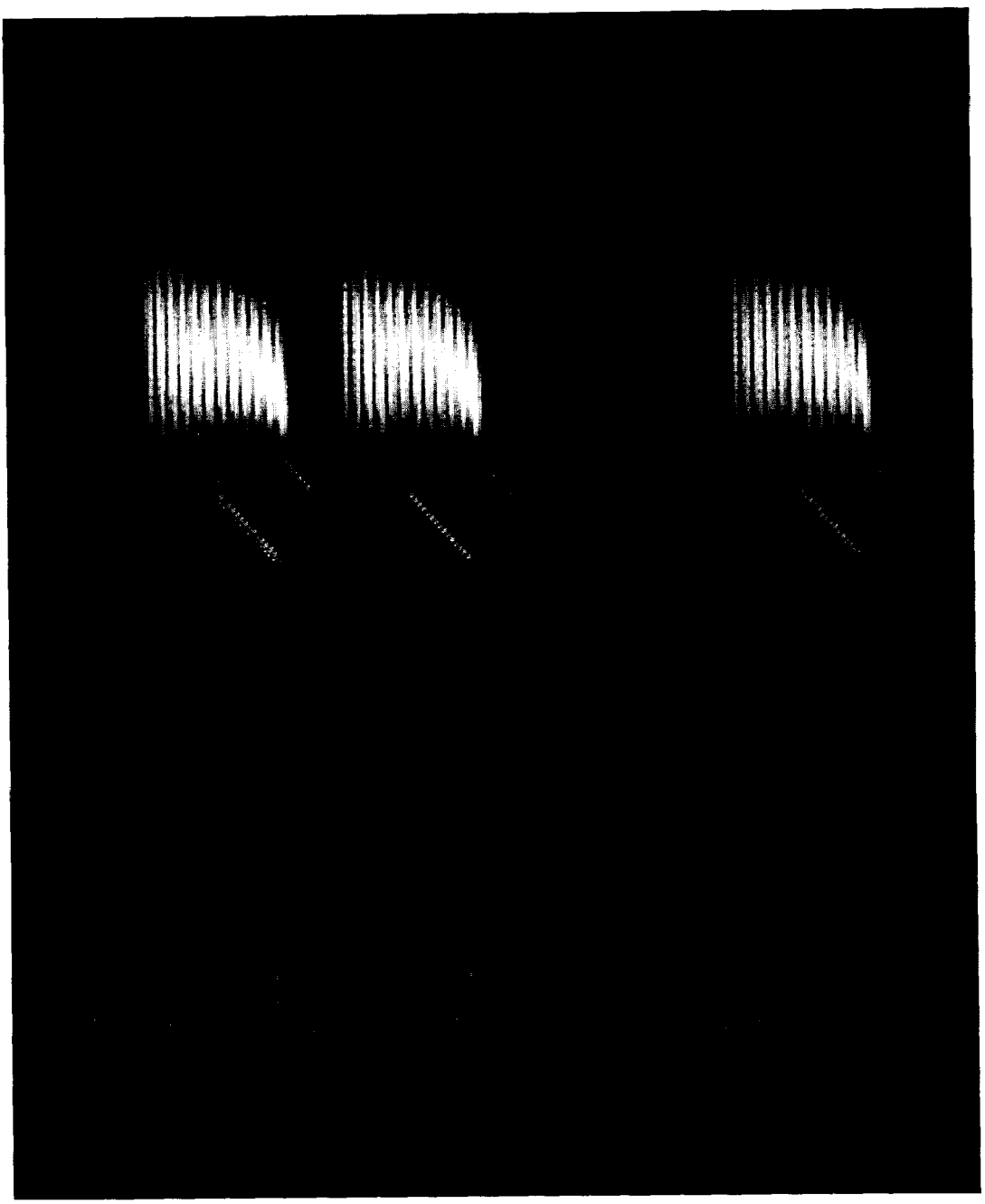
FIG. 9B is a phase contrast optical image of three suspended microfluidic channels.

An electron micrograph of three suspended microchannels is shown in FIG. 9*a*, and a phase contrast optical image is shown in FIG. 9*b*. To obtain continuous fluidic delivery to the suspended channels, a microfluidic network made of poly(dimethylsiloxane) (PDMS) was bonded to the chip surface. The inlets to the nitride channels were located within U-shaped channels in the PDMS so that solutions could be transported with low flow resistance to the low-volume microchannels. The device was actuated electrostatically, and the deflection was measured with the optical lever method. Good electrical conductivity and high optical reflectivity were achieved by coating the suspended channels with a 100 nm aluminum thin film. The aluminum was connected to ground, and a drive electrode was brought to within 50 µm of the device by means of a micrometer stage.

Frequency responses were recorded using a function generator in frequency sweep mode and a lock-in amplifier. To obtain time-plots of the resonance frequency, the device was placed in a feedback loop, with the output of the deflection sensor connected directly to the drive electrode via a saturating voltage amplifier with ±5V output swing. The drive signal was offset by +60V with respect to ground, and the oscillation frequency was measured by means of a frequency counter. In this configuration we observed a frequency noise level of 80 mHz rms in a 4 mHz to 4 Hz measurement bandwidth.

Figure 10:
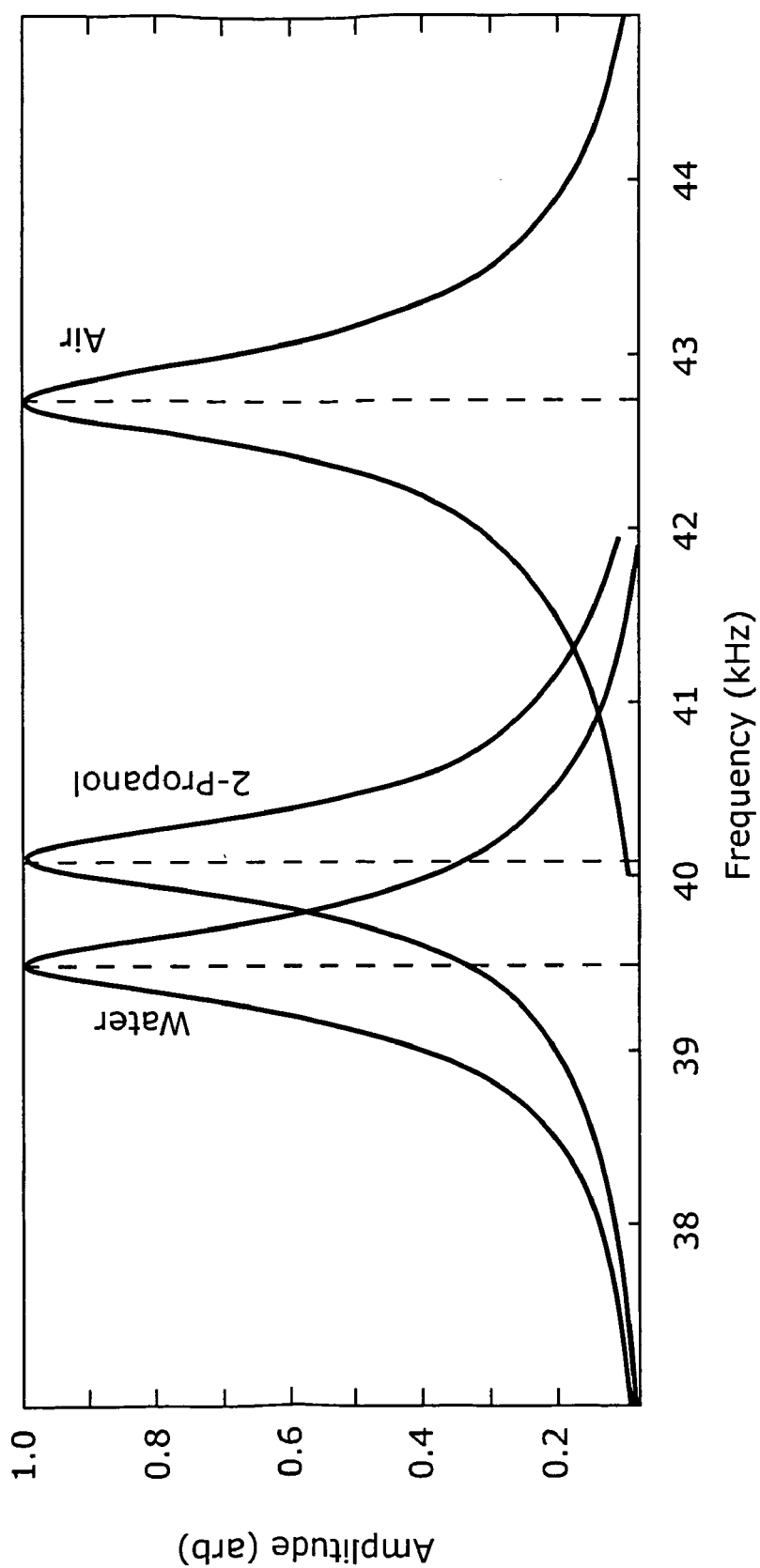
FIG. 10 are normalized frequency response curves of a 300 μm long cantilever filled with air, 2-propanol and water.

In order to evaluate the mass resolution, we measured the frequency response for a 300 µm cantilever in the unfilled state, as well as filled with isopropyl alcohol, and filled with water. The resulting spectra are shown in FIG. 10. Note that the quality factor in each remains the same which indicating that energy loss of a fluid-filled microchannel is not increased by the viscous drag associated with the solution enclosed in the microfluidic channels. This is because the small volume of the microchannel (~27 pL) and the small vibration amplitude (<<1 µm) results in very few water molecules being transferred during each oscillation cycle.

Taking into account the known mass densities of the different media and the design volume of 27 pL, we find a mass sensitivity of 107 mHz/pg for small loadings of a water filled microchannel. Given this sensitivity together with the 80 mHz noise level and a surface area of 53000 µm$^2$, our current detection limit is approximately $1.4 \times 10^{-17}$ g/µm$^2$ over a 4 mHz to 4 Hz bandwidth.

Figure 11:
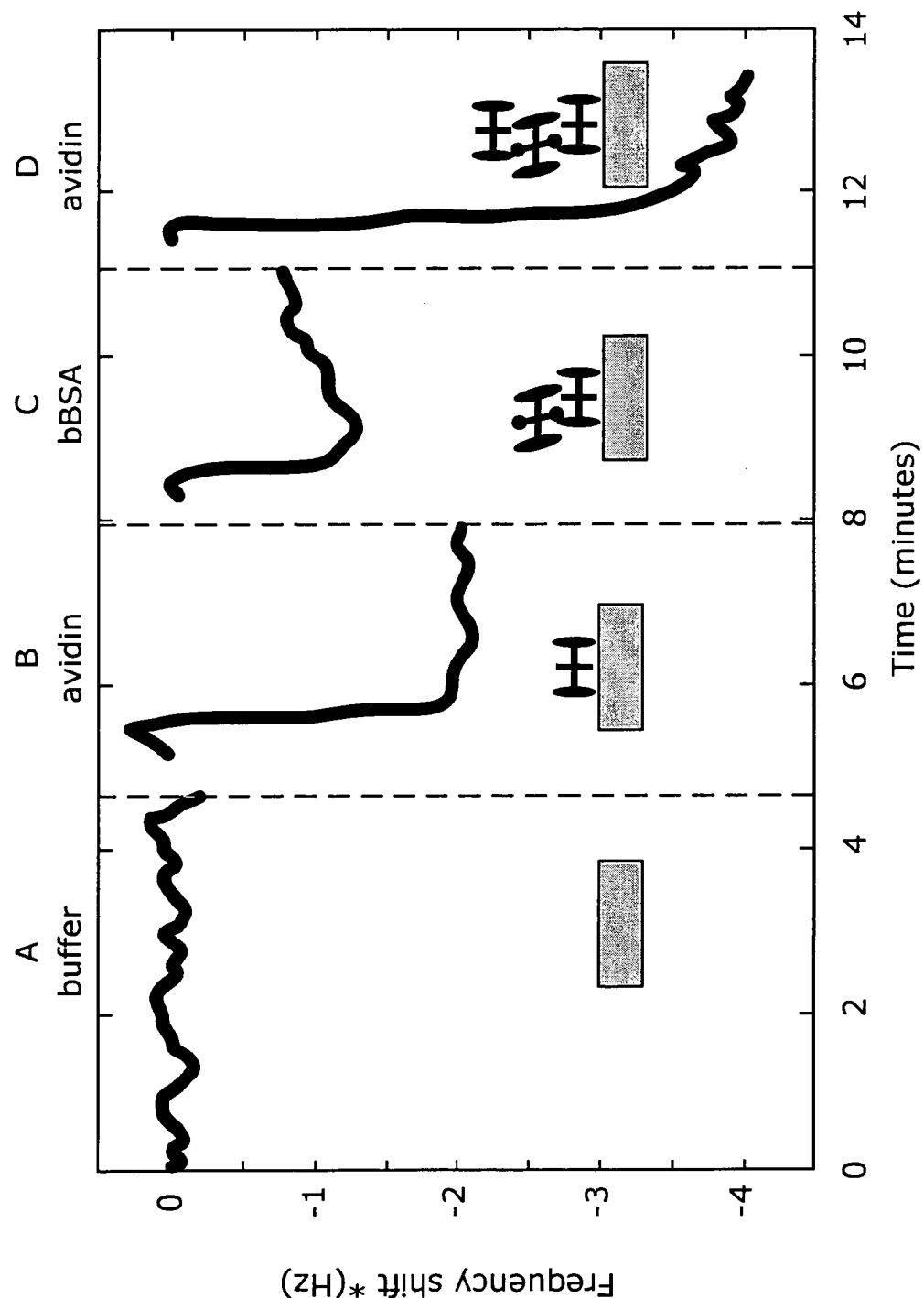
FIG. 11A-D are the relative frequency shift for a 40 kHz resonant microfluidic channel after injection of (A) buffer, (B) avidin, (C) bBSA, and (D) avidin.

We demonstrated biomolecular detection by functionalizing the interior channel walls with biotinylated Bovine Serum Albumin (bBSA) and performing several experiments to detect the subsequent binding of avidin and bBSA. Constant fluid pressure was maintained at all times, except during the switching between reagents. Avidin and bBSA were dissolved in phosphate buffered saline (PBS) at 500 µg/mL and 1 mg/mL, respectively. The results of these experiments are summarized in FIG. 11. Each section represents the relative frequency shift over time, zeroed at the point at which fluids were switched. FIG. 1A shows the baseline signal after disconnecting and reconnecting buffer. FIG. 11B is the result of switching from buffer to avidin solution. The resonance frequency dropped sharply by more than 2 Hz a few seconds after changing fluids. This delay was expected due to the time required for the liquid to flow from the point of switching to the beginning of the suspended channel. When we switched back to buffer, the resonance frequency remained unchanged, indicating that fluid density difference did not cause the signal. Next, we verified that the frequency also remained unchanged when we re-injected avidin into the buffer filled microchannel. This suggests that all available binding sites for avidin had already been occupied. Next, we switched to bBSA solution, followed again by avidin. In both cases, a rapid drop in resonance frequency could be observed (FIGS. 11C and 11D). The fact that the injection of bBSA restored the ability to detect avidin in the resonating microchannel can be explained by bBSA-avidin multilayer formation, as illustrated schematically in FIG. 11. Since there are several biotins attached to each BSA molecule, a new bBSA layer can provide many binding sites for the subsequent adsorption of avidin.

None of the binding and control experiments described previously revealed frequency shifts from changes in volumetric density between buffer and bBSA or avidin. Although we estimate that these solutions should shift the frequency by a few hundred millihertz, we found that the complete exchange of fluid within the suspended microchannel often required several minutes. Over this time-scale, frequency shifts below ~1 Hz would have been obscured by drift, which was often present. In contrast, the high binding affinity of biotin-avidin results in rapid saturation of the surface concentration even at a fraction of the volume concentration that we injected.

Our results demonstrate that the relatively large surface area to volume ratio of the microchannel is advantageous for mass detection. Once a dilute sample enters the microchannel, the molecules are quickly depleted as they bind to the immobilized capture ligand. As additional molecules enter, the surface soon collects many more molecules than are present in the surrounding solution. As a result, the enhanced channel concentration produces a measurable change in resonance frequency.

What is claimed is:

1. An apparatus comprising:
   at least one suspended beam wherein the beam encloses one or more sealed microfluidic channels, wherein each microfluidic channel has at least one inner surface that is treated with a capture ligand to bind to or react with at least one analyte; wherein the capture ligand is bound to the interior surface of the microfluidic channel; and wherein the beam is a resonating beam and the device measures changes in resonance frequency of the beam.

2. The apparatus of claim 1, further comprising a device for measuring a change in a mechanical property of the beam.

3. The apparatus of claim 2, wherein the device for measuring a change in the mechanical property of the beam is one or more capacitors.

4. The apparatus of claim 3, wherein the one or more capacitors are in contact with a surface of the beam.

5. The apparatus of claim 2, wherein the device measures the conductivity of the microfluidic channel.

6. The apparatus of claim 1, wherein the one or more microfluidic channels has a depth in the range of between about 100 nm and about 3000 nm.

7. The apparatus of claim 6, wherein the one or more microfluidic channels have at least one wall with a thickness in the range of between about 100 nm and 1200 nm.

8. The apparatus of claim 1, wherein the beam is suspended in a low pressure environment.

9. The apparatus of claim 1, wherein the beam is in a controlled environment.

10. The apparatus of claim 1, wherein the beam is a cantilever beam.

11. The apparatus of claim 1, wherein the beam is suspended between two mechanically stable supports.

12. An apparatus comprising:
at least one suspended beam wherein the beam encloses one or more sealed inicrofluidic channels, wherein each inicrofluidic channel has at least one inner surface that is treated with a capture ligand to bind to or react with at least one analyte; wherein the one or more microfluidic channels further comprises a gel and the capture ligand is bound to the gel; and
wherein the beam is a resonating beam and the device measures changes in resonance frequency of the beam.

13. The apparatus of claim 12, wherein the beam has two mierofluidic channels that meet in a region containing a polymerized gel then separate downstream from the gel.

14. The apparatus of claim 13, wherein the analyte is transportable into the gel via pressure from the fluid flow.

15. The apparatus of claim 1 or 12, wherein the resonance of each beam is driven by a pair of drive electrodes.

16. The apparatus of claim 15, wherein the drive electrodes are also used to measure a change in the mechanical property of the beam.

17. The apparatus of claim 15, wherein one of the electrodes of the electrode pair is common to all the beams and the other electrode of the electrode pair is separately addressable for each beam.

18. The apparatus of claim 17, wherein the common electrode is in contact with the each beam.

19. The apparatus of claim 17, wherein the common electrode is an electrolyte solution in the microfluidic channel.

20. The apparatus of claim 17, wherein the electrodes are a metal that is, independently, selected from the group consisting of gold, nickel, platinum, aluminum, copper, antimony, tin, indium, chromium, titanium, and alloys thereof.

21. The apparatus of claim 20, wherein the electrodes are gold.

22. The apparatus of claim 1 or 12, wherein the capture ligand is a nucleic acid.

23. The apparatus of claim 22, wherein the capture ligand is a single stranded DNA.

24. The apparatus of claim 22, wherein the capture ligand is double stranded DNA.

* * * * *